United States Patent [19]

Maahs et al.

[11] 4,245,113
[45] Jan. 13, 1981

[54] PROCESS FOR THE MANUFACTURE OF 2,3,4,4-TETRACHLORO-3-BUTENOIC ACID ESTERS

[75] Inventors: Günther Maahs; Konrad Rombusch, both of Marl, Fed. Rep. of Germany

[73] Assignee: Chemische Werke Huels, A.G., Marl, Fed. Rep. of Germany

[21] Appl. No.: 19,204

[22] Filed: Mar. 9, 1979

[30] Foreign Application Priority Data

Mar. 10, 1978 [DE] Fed. Rep. of Germany ....... 2810397

[51] Int. Cl.³ .............................................. C07C 69/65
[52] U.S. Cl. .................................................. 560/219
[58] Field of Search ........................................ 560/219

[56] References Cited

U.S. PATENT DOCUMENTS

| 2,561,516 | 7/1951 | Ladd et al. | 260/111 |
| 2,985,684 | 5/1961 | Pennino | 560/219 |
| 3,803,189 | 4/1974 | Haglid | 260/429 R |

FOREIGN PATENT DOCUMENTS 2618557 11/1977 Fed. Rep. of Germany .

OTHER PUBLICATIONS

Maahs, G. Liebigs Ann. Chem. 686, 55 (1965).
Chemical Abstracts. vol. 63 (1965) #11373–11375 and index thereto.
Shelton, J. Reid et al., J. Org. Chem. 23, 1876–1880 (1958).

*Primary Examiner*—Natalie Trousof
*Assistant Examiner*—L. Hendriksen
*Attorney, Agent, or Firm*—Millen & White

[57] ABSTRACT

A process for preparing a 2,3,4,4-tetrachloro-3-butenoic acid ester comprises reacting tetrachlorocyclobutenone in the presence of hexachloro-1,3-butadiene with an alcohol at a temperature of 125°–200° C.

7 Claims, No Drawings

PROCESS FOR THE MANUFACTURE OF 2,3,4,4-TETRACHLORO-3-BUTENOIC ACID ESTERS

BACKGROUND OF THE INVENTION

It is known to react tetrachlorocyclobutenone with butanol at 120° C. to produce butyl 2,3,4,4-tetrachloro-3-butenoate (Liebigs Ann. Chem. 686, 55 (1965)). The tetrachlorocyclobutenone required as the starting material can be manufactured in a simple manner by a process which is not part of the prior art; specifically, by reacting (a) hexachlorocyclobutene with (b) anhydrous sulfuric acid and (c) sulfur trioxide; or with (b) anhydrous sulfuric acid and (d) phosphorus pentoxide at a temperature of 30°–140° C. The starting materials are present in the following molar ratios at the start of the reaction:

(a) : (c)=0.67 to 10,
(b) : (c)=0.1 to 10,
(a) : (d)=0.67 to 10 and
(b) : (d)=0.5 to 20.

This reaction is the subject of copending U.S. Application Ser. No. 019,204, filed on Mar. 9, 1979 whose disclosure is incorporated by reference herein.

Hexachlorocyclobutene, in turn, can be obtained by isomerization of hexachloro-1,3-butadiene (German Offenlegungsschrift No. 2,618,557). Because of the small difference in the boiling points of the two substances (4.7° C. at 67 mbars), this isomerization, which in general is carried out by distillation, requires an extremely high expenditure on apparatus. It is therefore considerably less expensive to instead work with mixtures of hexachlorocyclobutene and hexachloro-1,3-butadiene.

Since the reaction of hexachlorocyclobutene with, for example, fuming sulfuric acid (oleum) by the above-mentioned process proceeds equally well in the presence of hexachloro-1,3-butadiene as does the reaction of highly pure hexachlorocyclobutene, the less expensive mixture can be advantageously employed in preparing the tetrachlorocyclobutenone. However, of course, the result is a mixture of tetrachlorocyclobutenone and hexachloro-1,3-butadiene.

SUMMARY OF THE INVENTION

Accordingly, it is an object of the invention to provide a process for manufacturing 2,3,4,4-tetrachloro-3-butenoic acid esters from a mixture of tetrachlorocyclobutenone and hexachloro-1,3-butadiene with good yields and high selectivity.

Upon further study of the specification and appended claims, further objects and advantages of this invention will become apparent to those skilled in the art.

These objects have been achieved by this invention by providing a process for preparing a 2,3,4,4-tetrachloro-3-butenoic acid ester which comprises reacting tetrachlorocyclobutenone in the presence of hexachloro-1,3-butadiene with an alcohol at a temperature of 125°–200° C. This combination of measures is critical to the process.

DETAILED DISCUSSION

In no way could it have been expected that the reaction of tetrachlorocyclobutenone in the dilute state would proceed equally as readily as that of concentrated tetrachlorocyclobutenone. This can be seen from the following experiment.

If chlorine is allowed to act on a mixture of tetrachlorocyclobutenone and hexachloro-1,3-butadiene with the object of synthesizing pentachlorovinylacetyl chloride, it is observed that the selectivity falls sharply compared with that for the reaction of tetrachlorocyclobutenone of high percentage purity (>85 percent by weight). That is, it falls from about 90% of theory to just 60% of theory for a constant conversion of about 90%. This result is not changed even if the reaction temperature is raised from 120° to 140° C.

Similarly, the selectivity of the reaction of tetrachlorocyclobutenone with, for example, n-butanol at 120° C. falls from about 95% to about 45%, and the conversion falls from about 95% to 85% if a tetrachlorocyclobutenone which is only 22 percent pure is used in place of a 99 percent pure tetrachlorocyclobutenone. However, surprisingly, the selectivity and conversion of this reaction rise again to more than 95% if, under otherwise identical conditions, the reaction temperature is raised from 120° C. to 140° C.

It is thus surprising that, in accordance with this invention, the severe reduction in the selectivity of the reaction of tetrachlorocyclobutenone with alcohols at a temperature of 120° C., which is effected by the dilution of the tetrachlorocyclobutenone with hexachloro-1,3-butadiene, can be compensated by raising the reaction temperature to 125°–200° C.

The process of this invention is also surprising in that the elimination of RCL does not occur. This reaction is known to take place for highly pure esters of 2,3,4,4-tetrachloro-3-butenoic acid at elevated temperatures in accordance with the reaction equation

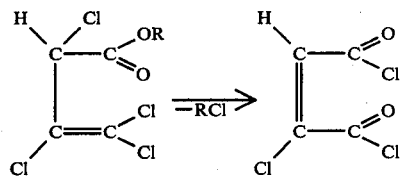

to give chloromaleic acid dichloride (Liebigs Ann. Chem. 688, 53 (1965)).

It is also surprising that, contrary to general experience, the selectivity and the conversion rise at the same time for the process of this invention.

Suitable mixtures of tetrachlorocyclobutenone and hexachloro-1,3-butadiene which can be employed in the process of this invention in general contain 10–85 percent by weight, and preferably 20–70 percent by weight, of tetrachlorocyclobutenone.

Suitable alcohols for conversion of the tetrachlorocyclobutenone, present as a mixture with hexachloro-1,3-butadiene, include those having up to 18 C atoms, preferably having 1–8 C atoms and particularly preferentially having 1–4 C atoms in an aliphatic or cycloaliphatic radical, which is optionally substituted by, for example 1–3 chlorine atoms or 1–3 alkyl groups thereby forming equivalent alcohols. Suitable alkyl and cycloalkyl groups include, for example, methanol, ethanol, propanol, iso-propanol, n-butanol, secbutanol, isobutanol, n-pentanol, n-hexanol, 2-ethylhexanol, n-octanol, n-nonanol, n-decanol, n-dodecanol, cyclohexanol, cyclododecanol, 3-chloropropanol and 4-chlorobutanol. Methanol, ethanol, n-propanol, iso-propanol and iso-butanol are preferred and n-butanol is particularly preferred.

The esterification reaction of this invention is carried out at temperatures of 125°–200° C., or 135°–200° C., and preferably of 135°–180° C. A temperature of 140°–170° C. is particularly preferred. Generally, 1–3 moles of alcohol are added per mole of tetrachlorocyclobutenone; preferably, stoichiometric amounts are employed. The order of addition of reactants and the use of agitation are not critical. Typically, reaction yields are 90–99% of theory and conversions are 90–99%. Depending on the boiling point of the alcohol employed, the reaction can be carried out under normal pressure, if appropriate, with the use of a reflux condenser, or under excess pressure.

A preferred embodiment of the reaction comprises initially introducing the mixture of tetrachlorocyclobutenone and hexachloro-1,3-butadiene into the reaction chamber; heating this to the desired temperature; and then gradually adding at least an equimolar amount of alcohol over a period of 5–240 minutes; and, in order to bring the reaction to completion, stirring the reaction mixture at the same temperature for at most an additional 120 minutes and preferably for an additional 5 to 60 minutes.

Of course, the hexachloro-1,3-butadiene does not participate in the esterification. However, most importantly, is also forms virtually no by-products. If it is not desired to make use of the 2,3,4,4-tetrachloro-3-butenoic acid ester product contained in the reaction mixture together with the hexachloro-1,3-butadiene, the latter can be separated off from the ester, which has a considerably higher boiling point, in a simple manner, e.g., by distillation. Of course, the crude ester present in the distillation residue can be used if desired. Alternatively, the distillation can be continued to obtain the pure ester.

The 2,3,4,4-tetrachloro-3-butenoic acid esters obtained can be used, optionally together with hexachloro-1,3-butadiene which has not been separated off, as activating co-catalysts in the manufacture of ethylene-α-olefinediene rubbers along with the so-called Ziegler-Natta catalysts, preferebly those based on vanadium compounds soluble in organic solvents, and ethylaluminum sesquichloride.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the Examples, the apparatus consisted fundamentally of a 250 cm$^3$ round-bottomed flask, which was fitted with a dropping funnel, a stirrer, a reflux condenser and a thermometer.

EXAMPLE 1

A mixture of 61.8 g (0.3 mole) of tetrachlorocyclobutenone (=30 percent by weight) and 144.2 g of hexachloro-1,3-butadiene was heated to 140° C. While maintaining this temperature, 22.3 g (0.3 mole) of n-butanol were then added dropwise over the course of 15 minutes and the reaction mixture was stirred for an additional 30 minutes. In addition to the hexachloro-1,3-butadiene which remained unchanged, the reaction mixture contained 1.3 g of unconverted tetrachlorocyclobutenone and 81.1 g of n-butyl 2,3,4,4-tetrachloro-3-butenoate; that is, the selectivity was 98.5% of theory and the conversion was 97.9% of theory.

EXAMPLE 2

A mixture of 61.8 g (0.3 mole) of tetrachlorocyclobutenone (=50 percent by weight) and 61.8 g of hexachloro-1,3-butadiene was heated to 140° C. While maintaining this temperature, 22.3 g (0.3 mole) of n-butanol were then added dropwise over the course of 15 minutes and the reaction mixture was stirred for an additional 30 minutes. In addition to the hexachloro-1,3-butadiene, which had remained unchanged, the reaction mixture contained 0.32 g of unconverted tetrachlorocyclobutenone and 81.0 g of n-butyl 2,3,4,4-tetrachloro-3-butenoate; that is, the selectivity was 97.0% of theory and the conversion was 99.5% of theory.

It was possible to separate the reaction mixture by simple distillation under reduced pressure (0.3 mbar), by means of a small packed column, into a fraction containing 99.6 percent pure hexachloro-1,3-butadiene and a fraction of 98.5 percent pure n-butyl 2,3,4,4-tetrachloro-3-butenoate; the intermediate fraction which contained the two components in approximately equal proportions making up only about 1 percent by weight of the distillate.

EXAMPLE 3

A mixture of 20.0 g (0.096 mole) of 99 percent pure tetrachlorocyclobutenone (=50 percent by weight) and 20.0 g of hexachloro-1,3-butadiene was heated to 150° C. While maintaining this temperature, 3.2 g (0.1 mole) of methanol were then added dropwise over the course of 10 minutes and the reaction mixture was stirred for an additional 60 minutes. In addition to the hexachloro-1,3-butadiene, which had remained unchanged, the reaction mixture contained 0.56 g of unconverted tetrachlorocyclobutenone and 22.6 g of methyl 2,3,4,4-tetrachloro-3-butenoate; that is, the selectivity was 94.6% of theory and the conversion was 93.4% of theory.

EXAMPLE 4

A mixture of 20.0 g (0.096 mole) of 99 percent pure tetrachlorocyclobutenone (=50 percent by weight) and 20.0 g of hexachloro-1,3-butadiene was heated to 160° C. While maintaining this temperature, 3.2 g (0.1 mole) of methanol were then added dropwise over the course of 15 minutes and the reaction mixture was stirred for an additional 60 minutes. In addition to the hexachloro-1,3-butadiene, which had remained unchanged, the reaction mixture contained 0.1 g of unconverted tetrachlorocyclobutenone and 22.0 g of methyl 2,3,4,4-tetrachloro-3-butenoate; that is, the selectivity was 92.8% of theory and the conversion was 93.3% of theory.

EXAMPLE 5

A mixture of 10.0 g (0.048 mole) of 99 percent pure tetrachlorocyclobutenone (=50 percent by weight) and 10.0 g of hexachloro-1,3-butadiene was heated to 150° C. While maintaining this temperature, 4.54 g (0.048 mole) of 3-chloropropanol were then added dropwise over the course of 5 minutes and the reaction mixture was stirred for an additional 60 minutes. In addition to the hexachloro-1,3-butadiene which remained unchanged, the reaction mixture contained 0.1 g of unconverted tetrachlorocyclobutenone and 13.0 g of chloropropyl 2,3,4,4-tetrachloro-3-butenoate; that is, the selectivity was 90.6% of theory and the conversion was 99.0% of theory.

EXAMPLE 6

A mixture of 20.0 g (0.096 mole) of 99 percent pure tetrachlorocyclobutenone (=50 percent by weight) and 20.0 g of hexachloro-1,3-butadiene was heated to 165° C. While maintaining this temperature, 12.5 g (0.96 mole) of 2-ethylhexanol were then added dropwise over the course of 10 minutes and the reaction mixture was stirred for an additional 60 minutes. In addition to the hexachloro-1,3-butadiene which remained unchanged, the reaction mixture contained 34.1 g of ethylhexyl 2,3,4,4-tetrachloro-3-butenoate; that is, the selectivity was 99.0% of theory and the conversion was 99.5% of theory.

COMPARATIVE EXAMPLE 1

A mixture of 10.0 g (0.048 mole) of 99 percent pure tetrachlorocyclobutenone (=50 percent by weight) and 10.0 g of hexachloro-1,3-butadiene was heated to 120° C. While maintaining this temperature, 1.54 g (0.048 mole) of methanol were then added dropwise over the course of 5 minutes and the reaction mixture was stirred for an additional 30 minutes. In addition to the hexachloro-1,3-butadiene which remained unchanged, the reaction mixture contained 0.1 g of unconverted tetrachlorocyclobutenone and 2.7 g of methyl 2,3,4,4-tetrachloro-3-butenoate; that is, the selectivity was 23.9% of theory and the conversion was 99.5% of theory.

COMPARATIVE EXAMPLE 2

A mixture of 61.8 g (0.3 mole) of tetrachlorocyclobutenone and 61.8 g of hexachloro-1,3-butadiene was heated to 120° C. While maintaining this temperature, 22.3 g (0.3 mole) of n-butanol were then added dropwise over the course of 15 minutes and the reaction mixture was stirred for an additional 30 minutes. In addition to the hexachloro-1,3-butadiene which remained unchanged, the reaction mixture contained 9.4 g of unconverted tetrachlorocyclobutenone and 34.7 g of n-butyl 2,3,4,4-tetrachloro-3-butenoate; that is, the selectivity was 41.3% of theory and the conversion was 84.8% of theory.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing a 2,3,4,4-tetrachloro-3-butenoic acid ester which comprises reacting tetrachlorocyclobutenone in the presence of hexachloro-1,3-butadiene with an alcohol at a temperature of 125°–200° C.

2. The process of claim 1, wherein the starting mixture comprises a mixture of 10–85 percent by weight of tetrachlorocyclobutenone and 90–15 percent by weight of hexachloro-1,3-butadiene.

3. The process of claim 2, wherein the starting mixture comprises a mixture of 20–70 percent by weight of tetrachlorocyclobutenone and 80–30 percent by weight of hexachloro-1,3-butadiene.

4. The process of claim 1, wherein the reaction temperature is 135°–180° C.

5. The process of claim 4, wherein the reaction temperature is 140°–170° C.

6. The process of claim 1, wherein the alcohol is a $C_{1-18}$ aliphatic or cycloaliphatic alcohol.

7. The process of claim 1, which comprises first introducing a mixture of tetrachlorocyclobutenone and hexachloro-1,3-butadiene into a reaction chamber; raising the temperature of the mixture to 125°–200° C.; then adding the alcohol to the reaction chamber; while continuously stirring the reaction medium until the reaction has progressed to completion.

* * * * *